United States Patent
Winner

[11] 4,034,748
[45] July 12, 1977

[54] SPINAL RESTRAINT DEVICE

[76] Inventor: Stephen E. Winner, 4515 Tamarack Drive, Fort Wayne, Ind. 46815

[21] Appl. No.: 625,948

[22] Filed: Oct. 28, 1975

[51] Int. Cl.² .................................... A61F 5/04
[52] U.S. Cl. ......................... 128/87 R; 5/82 R
[58] Field of Search ............. 128/87, 84, 83, 133, 128/134; 5/82

[56] References Cited

U.S. PATENT DOCUMENTS

| | | | |
|---|---|---|---|
| 2,675,564 | 4/1954 | Hughes | 5/82 |
| 3,469,268 | 9/1969 | Phillips | 128/87 R X |
| 3,609,778 | 10/1971 | Zeiner | 5/82 |
| 3,724,453 | 4/1973 | Dixon et al. | 128/87 R |
| 3,737,923 | 6/1973 | Prolo | 5/82 |
| 3,897,777 | 8/1975 | Morrison | 128/83 X |

Primary Examiner—John D. Yasko
Attorney, Agent, or Firm—Albert L. Jeffers; Roger M. Rickert

[57] ABSTRACT

A spinal restraint device which consists of a board-like member which can be placed beneath a patient and secured to the patient as by straps and which includes a head immobilizer or restraint at the head end of the board-like member which is preferably inflatable and which can be placed against opposite sides of the head with the head immobilizer or restraint being secured to the head by a strap while the strap simultaneously secures the head to the board-like member.

The board-like member is preferably of a length which will extend from about the top of the head to about the crotch of a patient and, in addition to the strap in the head region of the board-like member, there is also a strap adapted to be engaged about the patient's chest and at least one further strap secured to the crotch end of the board-like member which can be drawn up through the crotch and secured to the chest strap providing for greater stability of the patient on the board-like member. The member is provided with hand holes so that it can be lifted and transported and, advantageously, has, on the underside, cleat elements which support the board-like member in spaced relation to a supporting surface such as the earth therebeneath.

2 Claims, 5 Drawing Figures

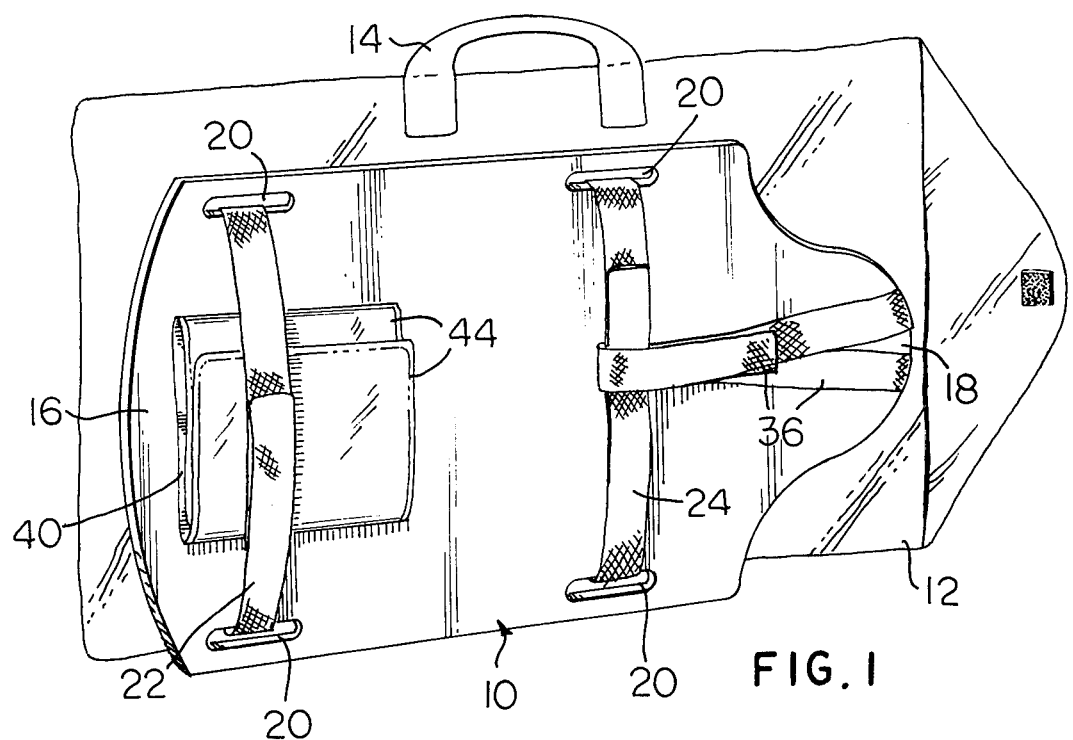
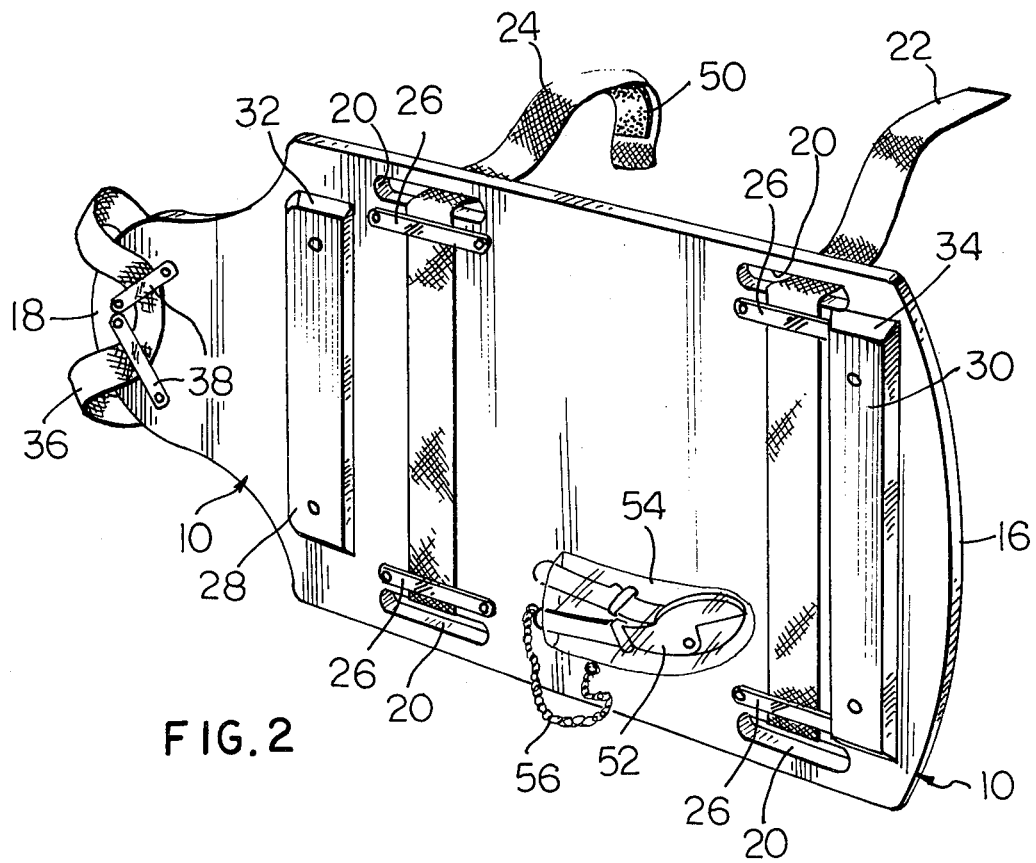

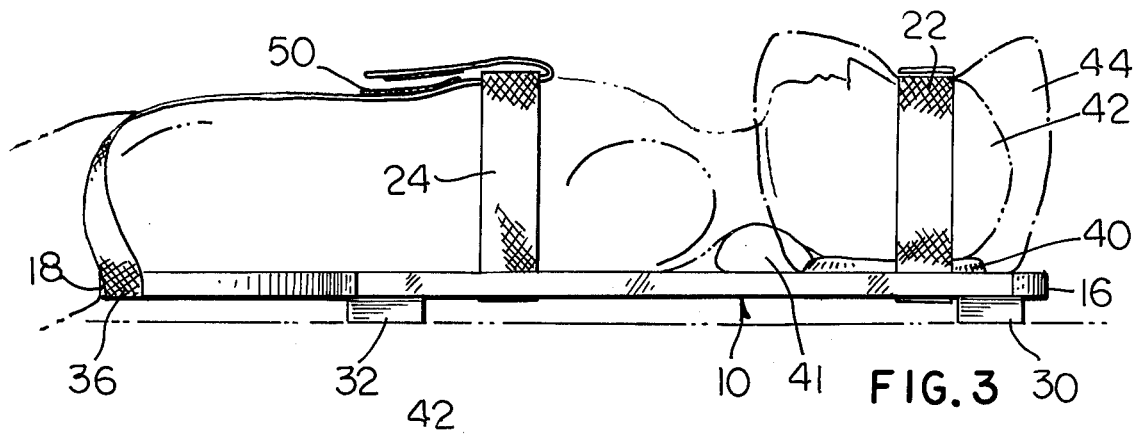
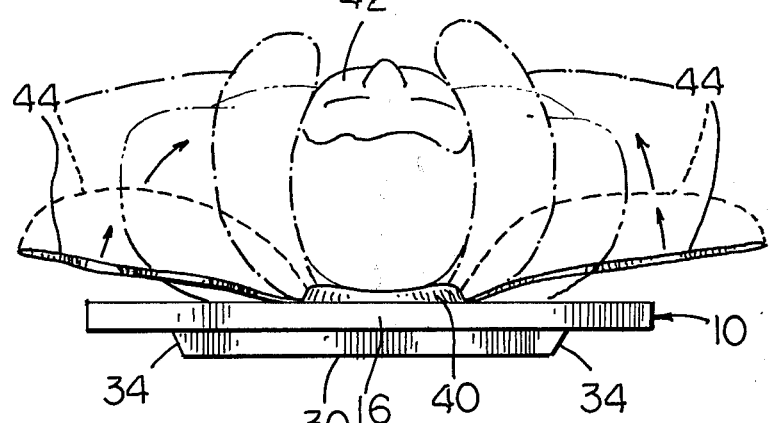
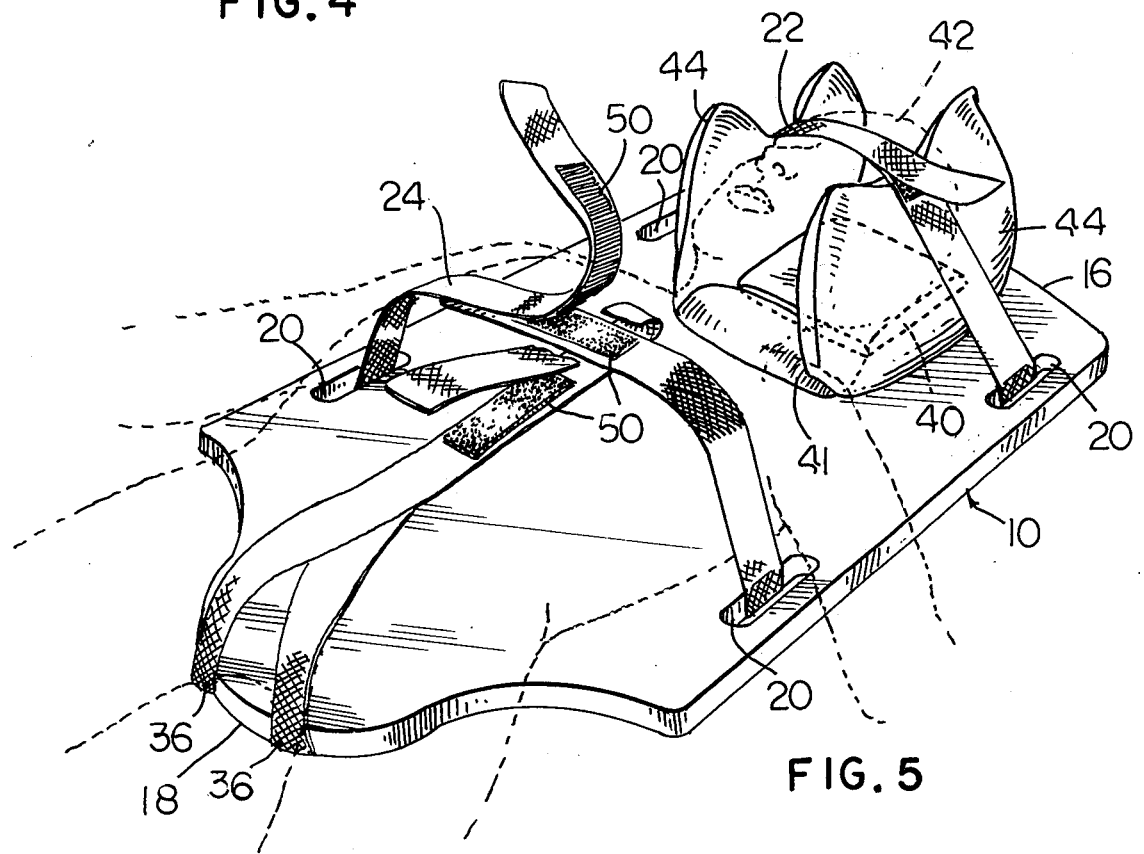

SPINAL RESTRAINT DEVICE

The present invention relates to a spinal restraint device and is particularly concerned with such a device especially constructed and arranged for use with emergency patients. Such an occasion might arise in the case of a player in an athletic event, such as football, becoming injured and requiring emergency treatment.

The treatment of emergency patients such as might be necessary in respect of an athletic casualty, such as an injured football player, requires considerable care. If the patient is suspected of having a head or cervical injury, it is not safe to remove the helmet from the player, and it is, also, important to prevent any substantial amount of movement of the player's head while he is being transferred to a place of treatment.

The helmets and face masks mounted on football players are relatively heavy and a properly fitted helmet is not easy to remove so that considerable hazard exists for the patient if it is attempted to remove the face mask or helmet, or both, to get to the mouth or throat area to establish a free airway for the patient or in case it became necessary to supply the patient with oxygen. Other emergency medical situations in which it is important to hold the spine an head of the patient in an immobile or restrained condition will suggest themselves.

The present invention solves the problems that can be encountered in a situation as referred to above by providing a device which can be introduced under the patient and which includes strap elements or the like for strapping the patient to the device while, furthermore, including a head immobilizing arrangement by means of which the patient's head can be substantially immobilized. The device then permits the patient to be lifted and transported to a place of treatment.

Especially for use of the device in connection with football players and the like who may be wearing head gear such as helmets and which may have face masks, the device advantageously has associated therewith a plier-like cutting tool by means of which the bars of a face mask or the like can be cut to expose the face region of the patient.

An object of the present invention is the provision of an improved litter or stretcher-like arrangement on which a patient can be placed and which is so constructed and arranged as to provide for spinal restraint and immobilization of a patient's head while the patient is being transported on the device.

Another object is the provision of a device of the nature referred to which is simple to use and which can rapidly be brought into use and which can be placed in a compact carrying case so as to be readily movable from one place to another.

BRIEF SUMMARY OF THE INVENTION

The device according to the present invention comprises a substantially flat board-like member which, when placed beneath the patient, will provide support for the entire length of the patient's spine and, advantageously, has hand holes along the side edges and cleats on the underneath side so that the hand holes can be grasped for lifting the device and conveying the patient to a place of treatment.

The device is preferably formed of a material transparent to x-rays so that at least preliminary x-rays can be taken without removing the patient from the device.

The board-like member may be formed of wood or a suitably strong plastic material, such as reinforced plastic, and has a length extending from about the top of the head to the region of the crotch and tapers inwardly at the crotch end. The head end of the board-like member carries a head immobilizer and this can take the form of a pad on which the head rests and wing-like elements connected to the opposite sides thereof so that they can be folded up against the sides of the head and which wing-like elements can advantageously be inflatable pneumatic members.

A separable strap element in the region of the head end of the board-like member can be used to strap the elements of the head immobilizer, or head restraint, to the sides of the patient's head while holding the patient's head on the board-like member. A further strap element spaced downwardly along the board-like member from the strap referred to above can be strapped about the patient's chest while a third strap element connected to the crotch end of the board-like member can be drawn upward throught the crotch and connected to the chest strap for further stabilizing the position of the patient on the board-like member.

Hand holes are formed along the side edges of the member, which can also serve as openings through which the strap elements for the head and chest pass, and the underneath side of the board-like member is provided with transverse cleats so that, under normal conditions, the board-like member is supported in spaced relation to the surface on which it rests thereby making it easier to grip the hand grips for lifting and transporting the patient.

The exact nature of the present invention will become more clearly apparent upon reference to the following detailed specification taken in connection with the accompanying drawings in which:

FIG. 1 is a perspective view showing the device according to the present invention in collapsed condition and a carrying case in which the device can be placed for transporting.

FIG. 2 is a perspective view looking at the underside of the device of the present invention.

FIG. 3 is a side view showing a patient secured to the device.

FIG. 4 is an end view looking in from the head end of the device showing how the head immobilizer or head restraint portion of the device is employed.

FIG. 5 is a perspective view showing a patient secured to the device.

DETAILED DESCRIPTION OF THE INVENTION

Referring to the drawings somewhat more in detail, the device according to the present invention comprises a board-like main member 10 which, when not in use, can be callapsed to a substantially flat condition and is then receivable in a carrying case 12 having handle 14 which will permit the device easily to be transported.

The board-like member 10 of the device can be formed of wood, or it can be formed of a reinforced plastic material, and is advantageously transparent to x-rays. Board-like member 10 has a head end 16 and a crotch end 18 and is of a length so as to reach from about the top of the head to about the crotch of an average person.

The device is provided with hand holes 20 along each side edge in longitudinally spaced relation by means of which the device can be grasped to lift it, and a patient thereon, in horizontal position for transporting of the patient to a place of treatment. The hand holes can be availed of for receiving the strap means 22 near the head end of the board-like member and strap means 24 spaced further down the board-like member in about the region of the chest of a patient on the board-like member. The strap means 22, 24 may consist of individual strap elements anchored to the underside of the board-like member as by the metal clamp strips 26, or each strap may be formed, as shown in FIG. 2, so as to be continuous from end to end.

The underside of the board-like member is provided with transverse cleats 28 and 30 on the underside which, at the end regions thereof at 32 and 34 are, preferably, bevelled, as will best be seen in FIG. 4 so that, if a patient is lying on the ground, the device can easily be slipped beneath the patient while the cleats will support the device with the main board-like member 10 in spaced relation to the surface beneath the device so that the device can easily be grasped by means of hand holes 20.

A further strap element 36 is secured to the crotch end of the board as by the metal strips 38 and is adapted for being drawn up through the crotch of the patient to stabilize the position of the patient on the device.

FIGS. 3, 4 and 5 disclose more in detail the manner in which the device is constructed and arranged and how it is used with a patient. An important feature of the device, which does not show in FIG. 2, is a pad 40 on the upper side of the board-like member 10 at the head end of the device and on which the head 42 of the patient is adapted to rest. Connected either to the board-like member 10 on opposite sides of pad 40 or to the side edges of pad 40 are a pair of flexible wing-like elements 44 which can be folded toward one another.

Advantageously, elements 44 are inflatable by supplying air thereto, via valve means not shown, and when inflated and folded upwardly from the FIG. 4 position thereof, will embrace the sides of the head of the patient as will be seen in FIGS. 3, 4 and 5.

The strap means 22 is arranged within the longitudinal region of the head immobilizing or head restraint elements 44 and when the two ends of the strap means 22 are brought together and connected together, the head restraint or head immobilizing elements 44 are firmly held against the sides of the patient's head while, also, the patient's head is held down against pad 40 thereby substantially immobilizing the patient's head.

It will be appreciated that the head restraint means is operative whether the patient is wearing a head gear or not due to the resilience and flexibility of the head restraint element 44. In either case, the patient's head is firmly held in position and is substantially immobilized.

The second strap means 24 is located in the chest region of the patient and is adapted for being drawn about the chest and the ends thereof secured together thereby substantially permitting movement between the chest region of the patient and the patient's head.

Finally, the strap means at 36 will be seen in FIG. 5 to be adapted to be drawn up through the patient's crotch and looped around the chest strap means 24 so that the position of the patient on the spinal restraint device is still further stabilized.

As will be seen in FIG. 5, the ends of the strap elements may be provided with complementary elements 50 of Velcro fabric. As is known, one element of Velcro fabric consists of fabric having a stiff closed loop pile and the other element consists of fabric having stiff hooks thereon which will hook into the closed loops of the other element when the fabric elements are brought together.

As will be seen in FIG. 2, a plier-like cutter tool 52 could be provided in a pocket 54 mounted on the underside of board-like member 10 and be connected to the board-like member by a flexible elements 56 so that, in cases where it might be necessary to cut through the bars of a face mask or the like, the cutting implement will be readily available.

The device can, also, advantageously include a neck support pad, at 41, adjacent head support pad 40.

Modifications may be made within the scope of the appended claims.

What is claimed is:

1. A body support comprising a planar elongate support member having a supporting length corresponding to the distance between the body head and the crotch; said member having first and second longitudinal edges;
    a resilient head support mounted at the head end of said member; a first strap portion being mounted to said first longitudinal edge opposite said head support and transversely wrappable over said head support; a second strap portion being mounted to said second longitudinal edge opposite said head support and transversely wrappable over said first strap portion; x-ray transparent means for releasable contact attachment between said first and second strap portions to hold the body head against said head support;
    a third strap portion being affixed to said first longitudinal edge of said member at a longitudinal position corresponding to the body chest and transversely wrappable over said member; a fourth strap portion being mounted to the second longitudinal edge oppositely said third portion and transversely wrappable over said member in registration with said third position; x-ray transparent means for releasable contact attachment of said third and fourth strap portions;
    said member having a supporting width corresponding to the body shoulder width; said supporting width extending between the body shoulder and waist; said member being contoured inwardly from a member position corresponding to the body waist to the crotch end of said member to provide unobstructed access to the body hips;
    a fifth strap portion having bifurcated spaced ends attached at said crotch end; said bifurcated ends flowing into a single strap member; said single strap member extendable longitudinally and wrappable around said third and fourth portions when said third and fourth portions are in attached relation; and said single strap member being doubled back over onto itself after wrapping around said third and fourth members; x-ray transparent means for releasable contact attachment of said single strap member when doubled back onto itself.

2. The apparatus of claim 1 including first and second elongate cleats mounted transversely to the underside of said member; said cleats having solid bevelled ends to provide for sliding insertion of said member between a body and a ground surface.

* * * * *